United States Patent [19]

Vinick

[11] 4,256,897
[45] Mar. 17, 1981

[54] PROCESS FOR THE PREPARATION OF L-ASPARTIC ACID N-THIOCARBOXYANHYDRIDE

[75] Inventor: Fredric J. Vinick, Waterford, Conn.

[73] Assignee: Pfizer Inc., New York, N.Y.

[21] Appl. No.: 89,641

[22] Filed: Oct. 29, 1979

[51] Int. Cl.³ .......................................... C07D 277/04
[52] U.S. Cl. ................................................... 548/183
[58] Field of Search ........................................ 548/183

[56] References Cited
U.S. PATENT DOCUMENTS 3,846,398  11/1974  Hirschmann et al. ............ 265/112.5

OTHER PUBLICATIONS

Dewey et al., J. Org. Chem. 36, 49, (1971).
Bailey, J. Chem. Soc. 1950, 3461, (1950).
Aubert et al., J. Chem. Soc. 1951, 2195, (1951).

*Primary Examiner*—Nicholas S. Rizzo
*Attorney, Agent, or Firm*—Francis X. Murphy; Charles J. Knuth; Peter C. Richardson

[57] ABSTRACT

An improved process for the preparation of L-aspartic acid N-thiocarboxyanhydride by the reaction of a 0.75 to 1.25 molar solution of an N-alkoxy-thiocarbonyl L-aspartic acid in a lower alkyl acetate solvent with a phosphorous trihalide. The desired product is substantially insoluble in the lower alkyl acetate solvent and is recovered in pure form without further purification or separation steps.

8 Claims, No Drawings

PROCESS FOR THE PREPARATION OF L-ASPARTIC ACID N-THIOCARBOXYANHYDRIDE

BACKGROUND OF THE INVENTION

This invention relates to the preparation of L-aspartic acid N-thiocarboxyanhydride, which is a useful intermediate for the synthesis of peptides. In particular, L-aspartic acid N-thiocarboxyanhydride is useful for reaction with L-phenylalanine lower alkyl esters to form L-aspartyl-L-phenylalanine lower alkyl esters, which are useful as potent sweetening agents for use in food stuffs and beverages. The methyl ester is especially preferred as a sweetening agent.

The preparation of amino acid N-thiocarboxyanhydride derivatives is described in J. Org. Chem. 36, 49 (1971). One method of interest is by the reaction of an N-alkoxythiocarbonyl amino acid with a phosphorous trihalide. In order to allow the use of L-aspartic acid N-thiocarboxyanhydride as an intermediate for the preparation of L-aspartyl-L-phenylalanine lower alkyl esters for use in food products, it is necessary to be able to prepare the L-aspartic acid N-thiocarboxyhydride in good yields and in high purity.

SUMMARY OF THE INVENTION

In accord with the present process, it has now been found that by conducting the reaction of an N-alkoxythiocarbonyl-L-aspartic acid with a phosphorous trihalide in a lower alkyl acetate solvent, the desired L-aspartic acid N-thiocarboxyanhydride precipitates from the reaction solution when formed and can be readily recovered in good yields in highly pure form without the need for further separation and purification procedures. More particularly, the present invention provides a process for preparing L-aspartic acid N-thiocarboxyanhydride which comprises reacting a 0.75 to 1.25 molar solution of an N-alkoxythiocarbonyl-L-aspartic acid wherein said alkoxy group is of 1 to 3 carbon atoms, in an alkyl acetate solvent having from 1 to 4 carbon atoms in said alkyl group, with a phosphorous trihalide selected from phosphorous tribromide and phosphorous trichloride at a temperature from about −10° C. to 50° C., preferably 20° to 40° C., and recovering the solid L-aspartic acid N-thiocarboxyanhydride produced. Preferred lower alkyl acetate solvents are ethyl acetate and methyl acetate, most preferably ethyl acetate.

DETAILED DESCRIPTION OF THE INVENTION

L-Aspartic acid N-thiocarboxyanhydride is formed by the reaction of an N-alkoxythiocarbonyl-L-aspartic acid having from 1 to 3 carbon atoms in the alkoxy group and a phosphorous trihalide selected from phosphorous tribromide and phosphorous trichloride in accord with the following reaction scheme:

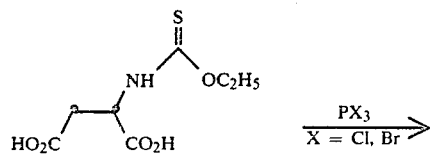

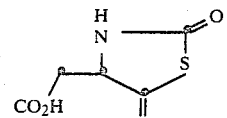

The N-alkoxythiocarbonyl-L-aspartic acid is readily prepared by means known in the art, for example by the reaction of L-aspartic acid and an appropriate methyl alkyl xanthate. Preferred N-alkoxythiocarbonyl-L-aspartic acids are the method and ethoxy derivatives.

The reaction of the N-alkoxythiocarbonyl-L-aspartic acid and the phosphorous trihalide is conducted in an alkyl acetate solvent, the alkyl group having from 1 to 4 carbon atoms, preferably ethyl acetate or methyl acetate, most preferably ethyl acetate. Sufficient alkyl acetate solvent is employed so as to provide an initial concentration of the N-alkoxythiocarbonyl-L-aspartic acid from about 0.75 molar to about 1.25 molar, preferably between about 1.0 and 1.25 molar. The N-alkoxythiocarbonyl-L-aspartic acid and phosphorus trihalide reactants are soluble in the alkyl acetate solvent, but the L-aspartic acid N-thiocarboxyanhydride product is substantially insoluble therein and precipitates from solution in highly pure form as soon as it is formed in the reaction. As a result, the use of such alkyl acetate solvents provide an improved, economic and simple process whereby pure L-aspartic acid N-thiocarboxyanhydride is obtained in high yields, without the need for complex recovery and purification procedures necessary in other solvents where the L-aspartic acid N-thiocarboxyanhydride has greater solubility. Further, such alkyl acetate solvents are suitable for use in large scale commercial production of the desired L-asparticd acid N-thiocarboxyanhydride and avoid the problems associated in the use of more volatile reaction solvent such as diethyl ether.

The phosphorous trihalide is selected from phosphorous trichloride and phosphorous tribromide, preferably phosphorus tribromide. From about 0.3 to about 0.5 moles of phosphorous trihalide per mole of N-alkoxythiocarbonyl-L-aspartic acid are employed, preferably from about 0.33 to about 0.4 moles. The reaction is generally conducted at a temperature from about −10° C. to about 50° C., preferably from about 20° C. to 40° C. The time necessary for completion of the reaction will vary depending on the reaction temperature but will generally be from about 5 minutes to about 1 hour.

The L-aspartic acid N-thiocarboxyanhydride is substantially insoluble in the alkyl acetate solvent and precipitates from solution as it is formed in the reaction. The desired product can therefore be readily recovered in pure solid form, for example, by filtration, preferably with cooling of the reaction solution to about −10° C. to about 5° C.

The L-aspartic acid N-thiocarboxyanhydride produced can be used directly without further purification in the formation of peptides, for example, in the preparation of L-aspartyl-L-phenylalanine lower alkyl esters useful as sweetening agents by reaction with L-phenylalanine lower alkyl esters. The amine acid coupling reaction is generally conducted at a pH from about 8 to 10, preferably about 9, at a temperature in the range about −10° C. to 40° C., preferably 0° C. to 10° C. The intermediate N-thiocarboxyanhydride dipeptide derivative formed is then converted to the desired L-aspartyl-L-phenylalanine lower alkyl ester by adjusting the pH of the reaction solution to about 2 to 6, preferably about 4.5 to 5.5. Applicant's copending U.S. Patent Application Ser. No. 89,640, filed concurrently herewith, provides a process for deodorizing such esters formed by this reaction.

The present invention is illustrated by the following examples. However, it will be understood that the invention is not limited to the specific details of these examples.

EXAMPLE 1

L-Aspartic acid (19.95 g, 0.150 mol) was suspended in 15 ml of water at 0° C., and 50% sodium hydroxide solution (24 g, 0.30 mol) was added dropwise with stirring. Methyl ethyl xanthate (22.44 g, 0.165 mol) in 15 ml of methanol was then added in one portion. The mixture was heated at 45° C. for 2 hours, cooled to room temperature, and washed with two portions of ethylene dichloride. The ethylene dichloride washes were discarded and the aqueous phase acidified with concentrated hydrochloric acid at 0° C. The solution was saturated with solid sodium chloride and extracted with two portions of ethyl acetate. The organic extracts were dried over anhydrous magnesium sulfate and evaporated in vacuo to afford 29.4 g (89%) of white crystalline N-ethoxythiocarbonyl-L-aspartic acid. mp 133° C.; nmr (DMSO-$d_6$) $\delta$1.23 (t, 3H, J=7 Hz), 2.67 (d, 2H, J=6 Hz), 4.37 (q, 2H, J=7 Hz), 4.93 (dt, 1H, J=6 Hz, 8 Hz), 9.26 (d, 1H, J=8 Hz).

EXAMPLE 2

L-Aspartic acid (571 g, 4.29 mol) was added gradually with stirring to 350.9 g (8.58 mol) of 50% sodium hydroxide solution at 0° C. Methyl methyl xanthate (550 g, 4.51 mol) in 405 ml of methanol was then added as rapidly as possible. The mixture was heated at 45° C. for 1.5 hours, cooled to room temperature, and washed with two portions of methylene chloride. The methylene chloride washes were discarded and the aqueous phase acidified with concentrated hydrochloric acid at 0° C. The solution was extracted with three portions of ethyl acetate, and the combined extracts washed with brine and dried over anhydrous magnesium sulfate. The solvent was evaporated in vacuo to give a yellow oil which crystallized upon addition of ethylene dichloride and n-hexane. The N-methoxythiocarbonyl-L-aspartic acid was collected by filtration, washed with fresh n-hexane, and dried (420 g, 47%). mp 128°–130° C.; nmr (DMSO-$d_6$) $\delta$2.73 (d, 2H, J=6 Hz), 3.63 (s, 3H), 4.43 (dt, 1H, J=6 Hz, 8 Hz), 6.63 (d, 1H, J=8 Hz); ir (KBr) 1715, 1515 cm$^{-1}$.

EXAMPLE 3

N-Methoxythiocarbonyl-L-aspartic acid (207.0 g, 1.00 mol) was dissolved in 1200 ml ethyl acetate at 0° C., and phosphorous tribromide (47 ml, 0.50 mol) was added in one portion. The cooling bath was removed and the temperature allowed to rise spontaneously to 35° C. The solution was stirred for 10 minutes after which time a granular white precipitate had formed. The reaction mixture was cooled to 0°–5°, and the product collected by filtration, washed with a small volume of ether, and dried. The yield of analytically pure L-aspartic acid N-thiocarboxyanhydride was 157.4 g (90%). mp 200°–205° C. (dec.); $[\alpha]_D^{25}$=109.5° (C=1, THF); ir (KBr) 3225, 1739, 1724, 1653, 1399 cm$^{-1}$; nmr (DMSO-$d_6$) $\delta$2.83 (d, 2H, J=5 Hz), 4.70 (t, 1H, J=5 Hz), 9.23 (bs, 2H, ex); MS m/e 175 (M+), 87, 60.

EXAMPLE 4

N-Methoxythiocarbonyl-L-aspartic acid (4.14 g, 20 mmol) was dissolved in 24 ml methyl acetate at 25° C., and phosphorous tribromide (0.66 ml, 7 mmol) was added in one portion. After 10 minutes the product was isolated as described in Example 3. The yield of pure L-aspartic acid N-thiocarboxyanhydride was 2.51 g (72%), identical in all physical and spectral properties with the material obtained in Example 3.

EXAMPLE 5

N-Methoxythiocarbonyl-L-aspartic acid (4.14 g, 20 mmol) was dissolved in 24 ml of n-butyl acetate at 25° C., and phosphorous tribromide (0.66 ml, 7 mmol) was added in one portion. After 10 minutes the product was isolated as described in Example 3. The yield of L-aspartic acid N-thiocarboxyanhydride was 3.10 g (89%).

EXAMPLE 6

Following the procedure of Example 3, N-methoxythiocarbonyl-L-aspartic acid (4.14 g, 20 mmol) was reacted with phosphorous tribromide (0.66 ml, 7 mmol) in 24 ml of isopropyl acetate. The yield of L-aspartic acid N-thiocarboxyanhydride was 83%.

EXAMPLE 7

Following the procedure of Example 3, N-methoxythiocarbonyl-L-aspartic acid (4.14 g, 20 mmol) was reacted with phosphorous tribromide in 24 ml of t-butyl acetate. The yield of L-aspartic acid N-thiocarboxyanhydride was 86%.

EXAMPLE 8

Following the procedure of Example 4, N-ethoxythiocarbonyl-L-aspartic acid (2.21 g, 10 mmol) was reacted with phosphorous tribromide (0.33 ml, 3.5 mmol) in 13.3 ml ethyl acetate. The yield of L-aspartic acid N-thiocarboxanhydride was 1.61 g (92%).

EXAMPLE 9

Following the procedure of Example 4, N-ethoxythiocarbonyl-L-aspartic acid (2.21 g, 10 mmol) was reacted with phosphorous tribromide (0.33 ml, 3.5 mmol) in 8.3 ml ethyl acetate. The yield of L-aspartic acid N-thiocarboxyanhydride was 1.66 g (95%).

EXAMPLE 10

Following the procedure of Example 4, N-ethoxythiocarbonyl-L-aspartic acid (2.21 g, 10 mmol) was reacted with phosphorous tribromide (0.33 ml, 3.5 mmol) in 8.3 ml methyl acetate. The yield of L-aspartic acid N-thiocarboxyanhydride was 1.62 g (93%).

EXAMPLE 11

Following the procedure of Example 4, N-ethoxythiocarbonyl-L-aspartic acid (2.21 g, 10 mmol) was reacted with phosphorous tribromide (0.33 ml, 3.5 mmol) in 8.3 ml n-propyl acetate. The yield of L-aspartic acid N-thiocarboxyanhydride was 1.14 g (65%).

EXAMPLE 12

L-Phenylalanine methyl ester hydrochloride (108 g, 0.50 mol) was dissolved in 1000 ml water at 0°–5° C. and the pH of the solution adjusted to 9.0 with 50% sodium hydroxide solution. L-Aspartic acid N-thiocarboxyanhydride (91.9 g, 0.525 mol) was then added in portions with vigorous stirring; the pH was maintained at 8.9–9.1 by the addition of 50% sodium hydroxide solution as needed. Stirring and addition of hydroxide was continued until the pH stabilized at 9.0 (ca. 60 min). The pH was then adjusted to 5.0–5.5 with 12 N hydrochloric acid. Sufficient methanol was added to facilitate good stirring. The precipitated L-aspartyl-L-phenylalanine methyl ester was collected by filtration, washed with a small quantity of ice water, and dried. The isolated yield of product was 92 g (63%).

I claim:

1. A process for preparing L-aspartic acid N-thiocarboxyanhydride which comprises contacting a 0.75 to 1.25 molar solution of an N-alkoxythiocarbonyl-L-aspartic acid, wherein said alkoxy group is of 1 to 3 carbon atoms, in an alkyl acetate solvent having from 1 to 4 carbon atoms in said alkyl group, with a phosphorous trihalide selected from phosphorous tribromide and phosphorous trichloride at a temperature from about −10° C. to 50° C. and recovering the solid L-aspartic acid N-thiocarboxyanhydride produced.

2. A process of claim 1 wherein said solvent is ethyl acetate.

3. A process of claim 1 wherein said solvent is methyl acetate.

4. A process according to claim 1 wherein the phosphorous trihalide is phosphorous tribromide.

5. A process according to claim 1 wherein the temperature is between about 20° and 40° C.

6. A process according to claim 4 wherein said N-alkoxythiocarbonyl-L-aspartic acid is selected from N-methoxythiocarbonyl-L-aspartic acid and N-ethoxythiocarbonyl-L-aspartic acid.

7. A process according to claim 6 wherein said alkyl acetate is ethyl acetate and the reaction temperature is from about 20° C. to 40° C.

8. A process according to claim 7 wherein the L-aspartic acid N-thiocarboxyanhydride is recovered by filtration from said solution at −10° to 5° C.

* * * * *